US006342073B1

(12) United States Patent
Cumming et al.

(10) Patent No.: US 6,342,073 B1
(45) Date of Patent: Jan. 29, 2002

(54) INTRAOCULAR LENS FOR POSTERIOR VAULTING

(76) Inventors: J. Stuart Cumming, 1407 Emerald Bay, Laguna Beach, CA (US) 92651; Stephen G. Slade, 3900 Essex La. #101, Houston, TX (US) 77027

(*) Notice: Subject to any disclaimer, the term of this patent is extended or adjusted under 35 U.S.C. 154(b) by 0 days.

(21) Appl. No.: 09/474,861

(22) Filed: Dec. 30, 1999

(51) Int. Cl.[7] .................................................. A61F 2/16
(52) U.S. Cl. ............................... 623/6.46; 623/6.44
(58) Field of Search ........................... 623/6.11, 6.17, 623/6.22, 6.37–6.39, 6.43, 6.44, 6.46, 6.49, 6.51–6.54, FOR 105

(56) References Cited

U.S. PATENT DOCUMENTS 5,674,282 A * 10/1997 Cumming .................. 623/6.44

FOREIGN PATENT DOCUMENTS

FR      2 765 797    *   1/1999      623/FOR 105

* cited by examiner

Primary Examiner—David H. Willse
(74) Attorney, Agent, or Firm—Fulbright & Jaworski L.L.P.

(57) ABSTRACT

An intraocular lens has a lesser dimension longitudinally of haptics attached thereto than in the longitudinal direction to provide increased posterior vaulting for accommodation.

17 Claims, 1 Drawing Sheet

INTRAOCULAR LENS FOR POSTERIOR VAULTING

BACKGROUND AND SUMMARY OF THE INVENTION

The natural human lens effects accommodation, as between near and far vision, by ciliary muscle contraction and relaxation under brain control to dispose the lens in varying thicknesses at various locations along the axis of the eye.

The present invention provides improved, increased posterior vaulting of a lens optic by elongation of haptics disposed oppositely of the optic, while reducing the optic dimension in the longitudinal direction of the haptics.

Referring to FIG. 2 of the drawings, wherein the natural capsular bag is omitted for clarity, it will be understood from the geometrical relations of the ciliary muscle, the haptics and the optic, that the more elongated the haptics, the greater the posterior vaulting of lens haptics for accommodation.

The present invention provides an intraocular accommodating lens wherein an asymmetrical optic is of substantially greater dimension transversely of the longitudinal direction of haptics extending therefrom, and is of lesser dimension in the longitudinal direction of the haptics. With each haptic elongated to extend be tween the capsular bag equator and the optic, increased posterior vaulting of the optic is provided.

DESCRIPTION OF THE PREFERRED EMBODIMENT

Figure 1:
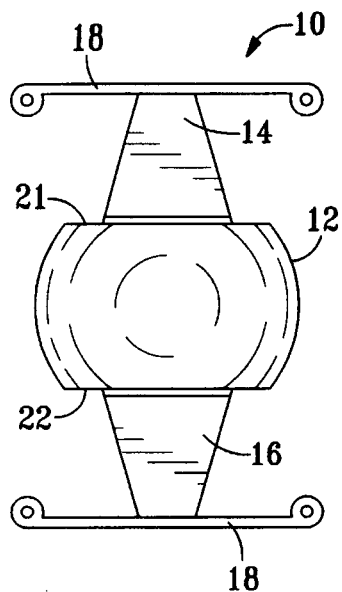
FIG. 1 is an elevational view of a preferred form of accommodating lens according to the invention.
Figure 2:
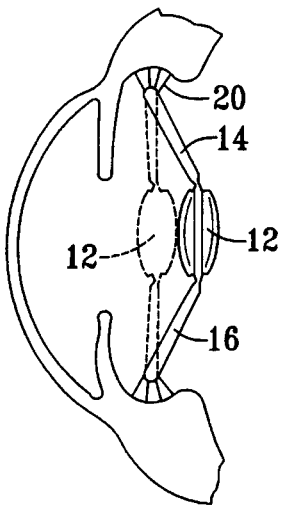
FIG. 2 is a sectional view of the lens of FIG. 1 disposed in an eye, showing the lens optic in a generally anterior position and in a posteriorly vaulted position.

Referring to the drawings, particularly FIGS. 1 and 2, a preferred embodiment 10 of the accommodating lens of the invention is shown as comprising an optic 12 and haptics 14, 16 extending oppositely therefrom and having loops 18 extending transversely thereof for engagement in the equator or rim of a capsular bag of an eye.

As shown, the lens is shortened in the longitudinal direction of haptics 14, 16 extension and elongated in the transverse direction, and the haptics are elongated in the longitudinal direction. From the geometry of the features and components, including the ciliary muscle 20, the haptics and the optic, it will be understood that the elongated haptics provide increased posterior vaulting of the optic, as indicated in FIG. 2.

The optic thus has a somewhat oval configuration, with flat straight portions 21,22 hinged to the haptics.

The lens of the invention provides improved, enhanced accommodation by increased posterior vaulting of the optic, while maintaining a maximal optical zone for accurate vision.

The optic 12, while relatively wide and enlarged in the direction transverse to the longitudinal direction of the haptics, and relatively short in the longitudinal direction, nevertheless has a full optical zone to provide full optical effect transmitted to the retina of the eye.

Whereas artificial intraocular lenses typically have optical zones of less than 5.0 mm in diameter, particularly lenses with haptics staked into optics, the present invention provides optical zones of about 6.0 mm transversely and about 4.5 mm longitudinally.

Figure 3:
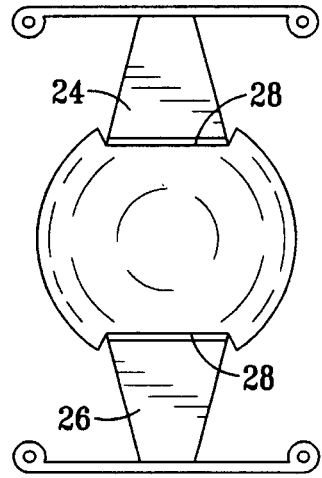
FIG. 3 is an elevational view of another preferred embodiment.
Figure 4:
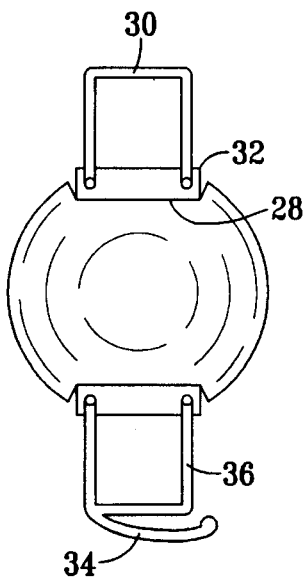
FIG. 4 is an elevational view of another embodiment.

FIGS. 3 and 4 show embodiments of the invention wherein generally circular optics have indented linear portions 28, to which haptics 24, 26 are hingedly connected.

FIG. 4 shows a lens with indentations 28 at which are hingedly mounted haptics of generally rectilinear rod-like configuration, the haptics having plate elements 32 hingedly mounted to the optic.

FIG. 4 also illustrates a loop haptic portion 34 extending transversely from an outer edge portion of a haptic 36 to aid in centering the lens within the capsular bag of the natural human lens. A haptic 30 without a loop haptic portion 34 in mounted on the other side of the lens.

Figure 5:
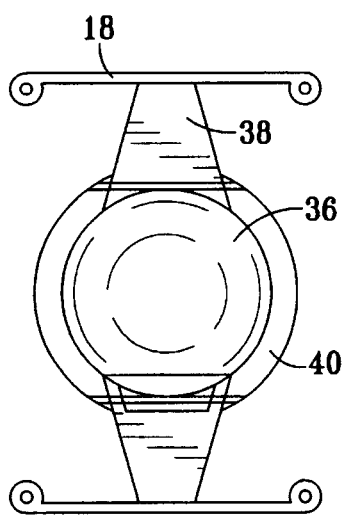
FIG. 5 is an elevational view of another embodiment wherein a generally annular glare-reducing component is disposed about an optic.

FIG. 5 shows an embodiment wherein haptics are hingedly mounted relative to an optic, and disposed about an optic 36 is a thin, annular transparent or translucent light-transmitting member 40 which reduces edge glare imposed on the retina.

It will be understood that various changes and modifications may be made from the preferred embodiment discussed above without departing from the scope of the present invention, which is established by the following claims and equivalents thereof.

What is claimed is:

1. An intraocular accommodating lens having haptics extending in a longitudinal direction between opposite portions of the equator of a capsular bag of an eye, said lens comprising:
   an asymmetrical optic of substantially greater dimension transversely of said longitudinal direction and of lesser dimension in said longitudinal direction, and
   haptics extending oppositely longitudinally from the optic to engage the equator of the capsular bag, said haptics having such lengths as to extend from respective capsular bag equator portions to attachment at opposite portions of the optic,
   whereby increased posterior vaulting of the optic is provided by elongated haptics,
   further including the optic having linear edge portions at longitudinally opposite sides thereof, and said haptics being hinged to said opposite linear portions,
   wherein said linear edge portions are indented from the periphery of the optic to enable elongation of the haptics.

2. An intraocular accommodating lens according to claim 1, wherein the optic comprises a full optical zone provided by the transverse extension of the optic.

3. A lens according to claim 1, wherein said optic has a longitudinal dimension of about 4.5 mm and a transverse dimension of about 6.0 mm.

4. A lens according to claim 3, wherein said haptics have transversely extending peripheral loop portions for engagement in the capsular bag equator.

5. A lens according to claim 4, wherein said loop portions are formed of one of (a) polyimide, (b) prolene, (c) polymethyl methacrylate.

6. A lens according to claim 1, wherein the haptics are hingedly mounted to the optic by flexible portions thereof adjacent to the optic.

7. A lens according to claim 1, wherein the haptics are hinged to the optic by grooved hinged portions of the haptics adjacent the optic.

8. A lens according to claim 1, wherein said optic is formed of one (a) silicone, (b) acrylic, (c) hydrogel, (d) PMMA, (e) other optically clear material.

9. A lens according to claim 1, and further including:

a light-transmitting skirt disposed about at least a portion of the periphery of the optic for reduction of glare impinging upon the retina of the eye.

10. An intraocular accommodating lens having haptics extending in a longitudinal direction between opposite portions of the equator of a capsular bag of an eye, said lens comprising:

an asymmetrical optic of substantially greater dimension transversely of said longitudinal direction than in said longitudinal direction, said optic being sized to provide a full optical zone, said optic having generally linear opposite edge portions extending transversely at opposite edges thereof, and plate haptics joined to the optic at said linear edge portions, and extending oppositely longitudinally of the optic to engage opposite capsular bag equator portions, whereby enhanced posterior vaulting of the optic is provided by elongated haptics, wherein said linear edge portions are indented from the periphery of the optic to enable elongation of the haptics.

11. A lens according to claim 10, wherein said optic has a longitudinal dimension of about 4.5 mm and a transverse dimension of about 6.0 mm.

12. A lens according to claim 11, wherein said haptics have transversely extending peripheral loop portions for engagement in the capsular bag equator.

13. A lens according to claim 12, wherein said loop portions are formed of one of (a) polyimide, (b) prolene, (c) polymethyl methacrylate.

14. A lens according to claim 10, wherein the haptics are hingedly mounted to the optic by flexible portions thereof adjacent to the optic.

15. A lens according to claim 10, wherein the haptics are hinged to the optic by grooved hinged portions of the haptics adjacent the optic.

16. A lens according to claim 10, wherein said optic is formed of one of (a) silicone, (b) acrylic, (c) hydrogel, (d) PMMA, (e) other optically clear material.

17. A lens according to claim 10, and further including:

a light-transmitting skirt disposed about at least a portion of the periphery of the optic for reduction of glare impinging upon the retina of the eye.

* * * * *

Dedication

6,342,073 B1—J. Stuart Cumming, Laguna Beach, CA (US); Stephen G. Slade, Houston, TX. INTRAOCULAR LENS FOR POSTERIOR VAULTING. Patent dated January 29, 2002. Dedication filed May 17, 2005, by the inventors, J. Stuart Cumming and Stephen G. Slade.

Hereby disclaims and dedicates to the Public all claims and entire term of said patent.

*(Official Gazette, November 8, 2005)*